(12) United States Patent
Sindhi

(10) Patent No.: US 10,371,696 B2
(45) Date of Patent: *Aug. 6, 2019

(54) MULTIPARAMETRIC METHOD FOR ASSESSING IMMUNE SYSTEM STATUS

(71) Applicant: University of Pittsburgh—Of the Commonwealth System of Higher Education, Pittsburgh, PA (US)

(72) Inventor: Rakesh Sindhi, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/678,994

(22) Filed: Aug. 16, 2017

(65) Prior Publication Data

US 2017/0343536 A1    Nov. 30, 2017

Related U.S. Application Data

(60) Continuation of application No. 15/432,858, filed on Feb. 14, 2017, now Pat. No. 9,772,326, which is a continuation of application No. 14/850,628, filed on Sep. 10, 2015, now Pat. No. 9,606,109, which is a continuation of application No. 14/278,306, filed on May 15, 2014, which is a division of application No. 13/847,252, filed on Mar. 19, 2013, now Pat. No. 8,759,016, which is a division of application No. 11/447,213, filed on Jun. 5, 2006, now Pat. No. 8,426,146.

(60) Provisional application No. 60/687,403, filed on Jun. 3, 2005.

(51) Int. Cl.
*G01N 33/483* (2006.01)
*G01N 33/50* (2006.01)
*C12Q 1/6809* (2018.01)
*G01N 33/569* (2006.01)
*G01N 33/53* (2006.01)

(52) U.S. Cl.
CPC ....... *G01N 33/5091* (2013.01); *C12Q 1/6809* (2013.01); *G01N 33/53* (2013.01); *G01N 33/56972* (2013.01)

(58) Field of Classification Search
None
See application file for complete search history.

(56) References Cited

U.S. PATENT DOCUMENTS

| | | | |
|---|---|---|---|
| 6,656,695 B2 | 12/2003 | Berg et al. | |
| 8,426,146 B2* | 4/2013 | Sindhi | C12Q 1/6809 435/7.2 |
| 8,759,016 B2* | 6/2014 | Sindhi | C12Q 1/6809 435/7.2 |
| 9,606,109 B2* | 3/2017 | Sindhi | C12Q 1/6809 |
| 2001/0016599 A1 | 8/2001 | Chun | |
| 2006/0062763 A1 | 3/2006 | Godfrey et al. | |
| 2006/0263343 A1 | 11/2006 | Kenyon et al. | |
| 2008/0241171 A1 | 10/2008 | Gentry et al. | |

OTHER PUBLICATIONS

Ozawa et al., An Appraisal of Pediatric Liver Transplantation from Living Relatives, Ann. Surg. Nov. 1992, pp. 547-553. (Year: 1992).*
Redchenko et al., Accessing Epstein-Barr Virus-Specific T-Cell Memory with Peptide-Loaded Dendritic Cells, Journal of Virology, Jan. 1999, pp. 334-342. (Year: 1999).*
Fujino et al., Differences in Lymphocyte Gene Expression Between Tolerant and Syngeneic Liver Grafted Rats, Liver Transplantation, vol. 10, No. 3, Mar. 2004, pp. 379-391. (Year: 2004).*
Ashokkumar et al., American Journal of Transplantation, 8: 1-12 (2008).
Assay Quality Control, 1-2 Retrieved on Jul. 13, 2009, from http://poultry-health.com/library/serodiss/assayqc/htm.
Demirkiran et al., "Low Circulating Regulatory T-Cell Levels After Acute Rejection in Liver Transplantation," Liver Transplantation, 12/2): 277-284 (Jan. 30, 2006).
Draper et al., Drug Metabolism Disposition, 26(4):305-312 (Apr. 1998).
Holzinger et al., "Are T Cells From Healthy Heart Really Only Passengers? Characterization of Cardiac Tissue T Cells," Immunology Letters, 53(2-3): 63-67 (Nov. 1996).
Klugewitz et al., "The Spectrum of Lymphoid Subsets Preferentially Recruited into the Liver Reflects that of the Resident Populations," Immunology Letters, 93(2-3): 159-162 (May 15, 2004).
Koyama et al. "Depletion of CD8 Memory T Cells for Induction of Tolerance of a Previously Transplanted Kidney Allograft," American Journal of Transplantation, 7:1055-1061 (2007).
Krowka et al., "Human T Cells in the SCID-hu Mouse are Phenotypically Normal and Functionally Competent," The Journal of Immunology, 146(11): 3751-3756 (Jun. 1, 1991).
Magill et al., "Donor-Specific Immunoreactivity can be Measured Rapidly by Proliferation of Activated, Memory T-Helper Cells in Flow Cytometric," CFSE-MLR 3rd International Congress on Immunosupression (Dec. 11, 2004).
Magill et al., "Rapid Detection of Donor-Specific Alloreactivity with Highly Activated Memory T-Helpers in CFSE-MLR with 7-Color Flow Cytometry," American Journal of Transplantation, Supplement 11, 5 (abstract 1161): 453 (May 21-25, 2005).
Nitta et al., "CFSE Dye Dilution Mixed Lymphocyte Reactions Quantify Donor-Specific Alloreactive Precursors in Non-Human Primate Cardiac Graft Rejection," Transplantation Proceedings, 33, pp. 326-329 (2001).

(Continued)

Primary Examiner — Gary Counts
(74) Attorney, Agent, or Firm — Klarquist Sparkman, LLP

(57) ABSTRACT

The invention provides a multiparametric method of assessing the reaction of a patient's immune system to a test subject. The invention compares a patient sample reacted with a test sample and a third party sample and combines the assessments of the multiple parameters to correlate the test reaction with a clinical event.

18 Claims, No Drawings

(56) References Cited

OTHER PUBLICATIONS

Palacios, "Epstein-Barr Virus increase the Proliferative Response and the Generation of Suppressor and Cytotoxic T-Cell Functions in Autologous Mixed Lymphocyte Reaction," *Scand. J. Immuno.* 17-24 (1982).

Sindi et al., "Enhanced Donor-specific Alloreactivity Occurs Independently of Immunosupression in Children with Early Liver Rejection," *American Journal of Transplantation*, 5: 96-102 (2005).

Tanaka et al., "Low Incidence of Acute Rejection After Living-Donor Liver Transplantation: Immunologic Analyses by Mixed Lymphocyte Reaction using a Carboxyfluorescein Diacetate Succinimidyl Ester Labeling Technique," *Transplantation*, 79(9): 1262-1267 (May 15, 2005).

Tanaka et al., "Multiparameter Flow Cytometric Approach for Simultaneous Evaluation of Proliferation and Cytokine-Secreting Activity in T Cells Responding to Allo-stimulation," *Immunological Investigations*, vol. 33, No. 3, pp. 309-324 (2004).

Yaffee et al., "Enhancement of Reliability Analysis: Application of Intraclass Correlations with SPSS/Windows v.8," (Mar. 11, 1998) Retrieved on Jul. 13, 2009 from http://www.nyu.its/statistics/Docs/intracls.html.

* cited by examiner

MULTIPARAMETRIC METHOD FOR ASSESSING IMMUNE SYSTEM STATUS

CROSS-REFERENCE TO RELATED APPLICATIONS

This application is a continuation of U.S. Patent application Ser. No. 15/432,858, filed on Feb. 14, 2017, issued as U.S. Pat. No. 9,772,326, which is a continuation of U.S. Patent application Ser. No. 14/850,628, filed on Sep. 10, 2015, issued as U.S. Pat. No. 9,606,109, which is a continuation of U.S. Patent application Ser. No. 14/278,306, filed May 15, 2014, abandoned, which is a divisional of U.S. Patent application Ser. No. 13/847,252, filed Mar. 19, 2013, issued as U.S. Pat. No. 8,759,016, which is a divisional of U.S. Patent application Ser. No. 11/447,213, filed Jun. 5, 2006, issued as U.S. Pat. No. 8,426,146, which in turn claims the benefit of U.S. Provisional Application No. 60/687,403, filed Jun. 3, 2005. The prior applications are all incorporated herein by reference in their entirety.

BACKGROUND OF THE INVENTION

The commonest early problems seen in transplant patients include rejection or side effects of anti-rejection drugs. This is observed in about half of all subjects. These complications remain a source of concern throughout the post-transplant course. Minimization of anti-rejection medications to alleviate side-effects presents a dilemma because it is attended by rejection in up to about one third of all patients. Moreover, as long as anti-rejection medications are used, transplant patients continue to experience a lifelong risk of life-threatening infections and cancers.

These complications result from the interplay of several factors, such as infectious agent or virus, transplanted tissue, host immune system, and anti-rejection drugs. The net effect that is seen as a clinical manifestation is therefore the result of multiple biochemical or molecular pathways that can be affected by these factors alone or in combination, to varying degrees. Current technology to assess such factors operates linearly, measuring one or only a few at a time. Such technology does not take into account the complexity of immune interactions. Thus, there is a need for the ability to monitor such multiple interrelated events and to deliver integrated output for clinical decision making.

BRIEF SUMMARY

The invention provides a multiparametric method of assessing the reaction of a patient's immune system to a test subject, who may be an organ donor or someone who is immunologically similar to the patient. The method includes: a) obtaining a first sample, a second sample, and a third sample from the patient, wherein the first sample and the second sample comprise lymphocytes, peripheral blood mononuclear cells (PBMCs), or a mixture of lymphocytes and peripheral blood mononuclear cells, and labeling the cells with a first marker or first set of markers, b) obtaining a test sample from a test subject, wherein the test subject is an individual other than the patient, and wherein the test sample comprises cells similar to the cells within the first sample obtained from the patient, and labeling the cells with a marker or set of markers, c) obtaining a third party sample from a third party, wherein the third party is an individual other than the patient and other than the test subject, and wherein the third party is immunologically dissimilar to the patient and the test subject, and wherein the third party sample comprises cells similar to the cells within the second sample obtained from the patient, and optionally labeling the cells with a marker or a set of markers, d) introducing the first sample obtained from the patient and the test sample obtained from the test subject into a first vessel under conditions sufficient for the cells within the first sample and the test sample to react, e) introducing the second sample obtained from the patient and the third party sample obtained from the third party into a second vessel under conditions sufficient for the cells within the second sample and the third party sample to react, wherein the second vessel is other than the first vessel, f) introducing the third sample obtained from the patient into a third vessel and subjecting it to similar conditions as the first and second vessel to serve as a control, g) measuring multiple parameters of the reaction in the first vessel to obtain a test measurement for each parameter, h) measuring multiple parameters of the reaction in the second vessel to obtain a third party measurement for each parameter, i) comparing each test measurement of a parameter to each third party measurement of the same parameter, whereby the test measurement is expressed as a fraction of the third party measurement to provide an assessment of the parameter, and j) combining the assessments of the multiple parameters to correlate the test reaction with a clinical event.

The invention also provides a multiparametric method of assessing the reaction of a patient's immune system to a test stimulant. The method includes: a) obtaining a first sample, and a second sample from the patient, wherein the first sample and the second sample comprise lymphocytes, peripheral blood mononuclear cells (PBMCs), or a mixture of lymphocytes and peripheral blood mononuclear cells, and optionally labeling the cells with a first marker or set of markers, b) subjecting the patient's first sample to stimulant in a first vessel under conditions sufficient for the patient's cells to react with the antigen, c) placing the patient's second sample into a second vessel under conditions similar to those of the first vessel to serve as a control, d) measuring multiple parameters of the reaction in the first vessel to obtain a test measurement for each parameter, e) measuring multiple parameters of the reaction in the second vessel to obtain a control measurement for each parameter, f) comparing each test measurement of a parameter to each control measurement of the same parameter, whereby the test measurement is expressed as a fraction of the control measurement to provide an assessment of the parameter, and g) combining the assessments of the multiple parameters to correlate the test reaction with a clinical event.

The invention further provides a multiparametric method of assessing the reaction of a test subject's immune system to a patient. The method comprises: a) obtaining a first sample, a second sample, and a third sample from the test subject, wherein the test subject is immunologically similar to the patient, and the first sample, second sample, and third sample comprise lymphocytes, peripheral blood mononuclear cells (PBMCs), or a mixture of lymphocytes and peripheral blood mononuclear cells, and labeling the cells with a marker or set of markers, b) obtaining a patient sample from the patient, wherein the patient's sample comprises cells similar to the cells within the first sample obtained from the patient, and optionally labeling the cells with a marker or set of markers, c) obtaining a third party sample from a third party, wherein the third party is an individual other than the patient and other than the test subject, and wherein the third party is immunologically dissimilar to both the patient and the test subject, and wherein the third party sample comprises cells similar to the cells within the second sample obtained from the patient, and optionally labeling the cells with a marker or a set of markers, d) introducing the first sample obtained from the test subject and the patient's sample obtained from the patient into a first vessel under conditions sufficient for the cells within the first sample and the patient's sample to react, e) introducing the second sample obtained from the test subject and the third party sample obtained from the third party into a second vessel under conditions sufficient for the cells within the second sample and the third party sample to react, wherein the second vessel is other than the first vessel, f) introducing the third sample obtained from the test subject into a third vessel and subjecting it to similar conditions as the first and second vessel to serve as a control, g) measuring multiple parameters of the reaction in the first vessel to obtain a test measurement for each parameter, h) measuring multiple parameters of the reaction in the second vessel to obtain a third party measurement for each parameter, i) comparing each test measurement of a parameter to each third party measurement of the same parameter, whereby the test measurement is expressed as a fraction of the third party measurement to provide an assessment of the parameter, and j) combining the assessments of the multiple parameters to correlate the test reaction with a clinical event.

The inventive methods and reagents can permit customized drug delivery targeted to the existing balance between the host immune system and its modulation by transplanted organ or infectious agent. The invention also can allow transplant patients to experience the benefits of anti-rejection drugs while minimizing the risk of side effects. These and other benefits, as well as additional inventive features, will be apparent from a review of the following detailed description.

DETAILED DESCRIPTION OF THE INVENTION

The invention provides a multiparametric immune system monitoring assay. The method measures multiple events at a single cell level, in target blood cells using flow cytometric techniques. These cells are participants in all immune responses toward a diverse range of stimuli such as transplanted (foreign) tissue, infectious agents such as viruses and bacteria, and drugs that affect the immune system as their intended (anti-rejection medications, medications for autoimmune states, and medications for allergies) or unintended (cancer drugs) target. Rare cellular subpopulations are identified by multiple identifiers, subjected to a simulated transplanted environment in a vessel, and are subsequently analyzed.

In one embodiment, the invention provides a multiparametric method of assessing the reaction of a patient's immune system to a test subject. The method includes: a) obtaining a first sample, a second sample, and a third sample from the patient, wherein the first sample and the second sample comprise lymphocytes, peripheral blood mononuclear cells (PBMCs), or a mixture of lymphocytes and peripheral blood mononuclear cells, and labeling the cells with a first marker or first set of markers, b) obtaining a test sample from a test subject, wherein the test subject is an individual other than the patient, and wherein the test sample comprises cells similar to the cells within the first sample obtained from the patient, and labeling the cells with a marker or set of markers, c) obtaining a third party sample from a third party, wherein the third party is an individual other than the patient and other than the test subject, and wherein the third party is immunologically dissimilar to the patient and the test subject, and wherein the third party sample comprises cells similar to the cells within the second sample obtained from the patient, and optionally labeling the cells with a marker or a set of markers, d) introducing the first sample obtained from the patient and the test sample obtained from the test subject into a first vessel under conditions sufficient for the cells within the first sample and the test sample to react, e) introducing the second sample obtained from the patient and the third party sample obtained from the third party into a second vessel under conditions sufficient for the cells within the second sample and the third party sample to react, wherein the second vessel is other than the first vessel, f) introducing the third sample obtained from the patient into a third vessel, which is other than the first and second vessel, and subjecting it to similar conditions as the first and second vessel to serve as a control, g) measuring multiple parameters of the reaction in the first vessel to obtain a test measurement for each parameter, h) measuring multiple parameters of the reaction in the second vessel to obtain a third party measurement for each parameter, i) comparing each test measurement of a parameter to each third party measurement of the same parameter, whereby the test measurement is expressed as a fraction of the third party measurement to provide an assessment of the parameter, and j) combining the assessments of the multiple parameters to correlate the test reaction with a clinical event.

Therefore, the invention provides a method for taking multiparametric measurements of the patient's sample, the test sample and the third party sample. Multiple parameters in each of these different samples can be assessed and therefore the interaction of the cells comprising the patient's immune system can be assessed.

The patient can be veterinary patient (e.g., small or large domestic animal) but more typically is a human child or adult. The patient can be an organ transplant candidate, or recipient or a non-organ transplant candidate or recipient. The patient can be undergoing treatment with an immunosuppressive regimen for a variety of conditions such as actual or suspected organ rejection, an autoimmune condition, or an allergic reaction. The patient can, for example, be undergoing treatment of an infectious disease.

A sample (e.g., first sample, second sample, third sample, etc.) can be any tissue drawn from the patient, test subject, or a third party. Typically, the sample will include white blood cells, preferably lymphocytes and/or PBMCs. Desirably, the first, second, and third samples drawn from the patient are substantially identical, and most preferably, the first second, and third samples are separate aliquots obtained from a common initial sample from the patient.

The test subject can be an organ donor, a candidate organ donor, an allergen, or other immunologically stimulating agent. When the test subject is an organ donor the donor can be an actual donor or a candidate donor. Moreover, the test subject can be a surrogate organ donor, if blood or tissue is unavailable from an actual donor or candidate donor. A surrogate donor desirably is immunologically similar at the class 1 and 2 major histocompatability loci to the actual donor. The donor should be immunologically compatible with the patient (as determined by similarity at the major histocompatibility antigen classes 1 and 2), can be living or deceased and the test sample obtained therefrom can be lymphocytes and other peripheral mononuclear blood cells obtained from blood taken from the donor, or tissue obtained from the donor's spleen. Preferably, donor cells are live, functioning cells, rather than cells that have been irradiated. When the test subject is an immunologically stimulating agent, other than that obtained from a donor, the test sample can additionally contain antigens such as autoantigens, peptides representing viral or bacterial antigens, antigen-attached to tetramers, and combinations thereof.

The third party can be a live subject or an allergen, or other immunologically stimulating agent. Where the third party is a live subject, (s)he should be immunologically dissimilar to the patient and the test subject, for example, as determined by similarity at the major histocompatibility antigen classes 1 and 2. The third party sample can include lymphocytes and other peripheral mononuclear blood cells or tissue obtained from the third party's spleen. When the third party is an immunologically stimulating agent, the sample can additionally contain antigens such as autoantigens, peptides representing viral or bacterial antigens, antigen-attached to tetramers, and combinations thereof.

In some embodiments, the cells of the test sample and the third party sample are labeled with a marker or set of markers before placing them in the vessel with the patient's samples to react. Such a marker or set of markers can be a specific marker antibody or marker dye that identifies the labeled cells. The marker can either be on the surface of the cells or within the cells, and it should stay with such cells for the life of the reaction. Alternatively, or in addition, the first, second, and third samples from the patients are similarly labeled. In instances in which both the cells from the patient and the cells with which the cells from the patient are to react (i.e., the test sample and the third party sample) are labeled, different markers or sets of markers preferably are used so as to distinguish the cells from the patient from those either from the test subject or third party.

In accordance with the present invention, the first and second samples from the patient are introduced into vessels (i.e., first and second vessels) with samples from the test subject and third party, respectively, under conditions sufficient for the cells in the vessels to react. Any suitable conditions can be used, but typically the cells are maintained in the vessel at about 37° C. for varying degrees of time so that they can react. Some reactions could be almost immediate, and the cells in the reaction could be assessed after a time of one or a few minutes. More typically, the period of time for the reaction is at least about 4 hours, or at least about 12 hours or overnight, and the reaction also can be run for one or several days. Preferably, the reaction is run for about 24 hours. As noted, the third sample from the patient is maintained under similar conditions as the test and third party reactions, so as to serve as a control for the culture conditions.

After the period of time set for the reaction of the cells from the test subject and the third party, the method involves measuring the multiple parameters. One type of the multiple parameters can be a physical characteristic of the cell. Physical characteristics can include cell size, complexity, and the degree of aggregation of the cells. In some embodiments, confounding cellular aggregates can be excluded from analysis and the parameters of single cells measured. In other embodiments, however, the degree of aggregation is itself a parameter that is assessed.

Another type of parameter that can be measured in the context of the inventive method is the cell type. Suitable cell types include lymphocytes and antigen-presenting cells, such as monocytes, dendritic cells, B-cells, macrophages, and the like. Cell subtype is another parameter that can be determined. Examples of cell subtypes include natural killer, T-helper and T-cytotoxic lymphocytes, as well as immunosuppressive or pro-inflammatory cells. Other cell types and subtypes can be used as parameters as desired.

Another type of parameter that can be measured in the context of the inventive method is the cells' functional state. Examples of functional states that can be measured include death, apoptosis, proliferation, cytokine producing, a particular stage in the cell cycle (e.g., $G_0$, $G_1$, $G_2$, etc.), for example using propidium iodide, degree of activity and whether the cells have memory or are naïve. Examples of the degree of cellular activity are highly activated, activated, and inactive. Types of memory include but are not limited to effector and central memory.

Another example of a cell function that can serve as a parameter to be measured in the context of the present invention is whether the cell produces one or more proteins such as cytokines. Cytokines can be inflammatory cytokines such as interferon gamma (IFN-gamma), tumor necrosis factor alpha (TNF-alpha), interleukin-2 (IL-2), interleukin-12 (IL-12) or combinations thereof. Cells that produce suppressive cytokines can also be detected. Examples of suppressive cytokines include but are not limited to interleukin 10 (IL-10), scurfin (FOXP3 gene product), transforming growth factor beta (TGF-beta), CTLA4, and combinations thereof. The presence, absence, amount or relative expression of any of the proteins described above and below, as well as other predetermined proteins can be measured.

Many of the measurements are made by taking advantage of protein biomarkers on the cells that indicate the above described parameters. Biomarkers useful in the inventive method include: CD3 (T-cell), CD4 (T-helper), CD8 (T-cytotoxic), CD19 (B-cell), CD11c (type 1 dendritic cell), CD123 (type 2 dendritic cell), CD14 (monocyte), CD45RO (memory), CD45RA (naïve), CD25high (highly activated), CD25low (activated), CD25negative (inactive), CD154 (antigen-specific activation), CSFElow (proliferative), annexin V (apoptotic), 7AAD (dead), CD27 (characterizes memory), CD28 (senescence), CD62 ligand (lymph node homing receptor), CD86 (costimulatory molecule), CD 69 (activation marker)), CD54 (costimulatory molecule), CD95 (fas ligand), CD71 (transferrin receptor), PD-1 (costimulatory molecule), PD1L (costimulatory molecule), ICOS (costimulatory molecule), CCR4 (chemokine receptor), CCR5 (chemokine receptor), CCR7 (chemokine receptor), CD16/56 (NK cell), ILT3 (inhibitory marker on antigen-presenting cells), HLA-DR, and combinations thereof. For example, markers that are specific to cell function include annexin V (apoptosis), active caspases, 7-AAD (death), CD25 (activation marker), CD69 (activation marker), CD71 (activation marker), CD86 (activation marker), and CD54 (activation marker). Examples of markers specific to cell differentiation include CD45RO, CD45RA, CD27, CD62 ligand, CD28, CCR4 (chemokine receptor), CCR5 (chemokine receptor), CD34, CD134, CD27, HLA-DR, CD11c, CD123, CTLA4, CD3, CD4, CD8, CD16/56, CD19, CD14, and ILT3.

In order to measure the above described physical and functional attributes, especially the presence and/or quantity of proteins, markers can be utilized to label the cells to be analyzed. Such markers typically are colored dyes that are able to be detected and differentiated by the flow cytometer. Marker dyes that persist in the cell can be used to distinguish one cell type from another in a mixed cell population. Examples of markers suitable for use with the present invention include: carboxyfluorescein diacetate succimidyl ester (CFSE, Molecular Probes, Eugene, Oreg.), EMA (cell viability dye), 7-AAD (cell viability dye) and Quantum dots, such as having emission spectra between 545 nm and 800 nm (Quantum Dot Corp., Hayward, Calif.). The use of such dyes is known in the art, and includes, for example, conjugating them to antibodies or other ligands for a specific protein. Compositions comprising these markers are also contemplated within the invention and can be used with the inventive method.

While any suitable equipment and methodology for measuring the multiple parameters can be employed, the preferred platform for measuring the multiple parameters is a flow cytometer. Flow cytometers capable of detecting and differentiating at least 4 (and more preferably at least 7) differently colored markers are preferred. More preferred is a flow cytometer capable of detecting and differentiating at least 10 and more preferably at least 19 or at least 25 differently colored markers. In fact, depending on the number of lasers in a flow cytometer, the inventive method is able to measure and compare in excess of 50 multiple parameters, such as in excess of 75 multiple parameters or even over 100 multiple parameters. The number of parameters which the inventive method can detect is limited by the number of lasers and detectors in such systems. In one embodiment, up to 240 lymphocyte subfamilies can be characterized simultaneously for the patient and test sample in each reaction mixture. Methods of using a flow cytometric machine are publicly available and are known to those in the art. Of course, while flow cytometers are preferred for use in the context of the present invention, some parameters can be measured using other methodology. For example, migratory behavior or cellular aggregation can be assessed using cell counters, microscopy, and other techniques.

In accordance with the inventive method, multiple parameters are measured in the reactions of the cells in the test reaction and the third party reaction. The unreacted third sample from the patient serves as a control. Desirably, the parameters are quantified to permit relative values to be determined between the test reaction and the third party reaction. Thus, for each parameter, the patient-test subject reaction can be expressed as a fraction (ratio) of the patient-third party reaction, and the battery of multiple ratios can then serve as a basis for addressing the relevance of the reaction to the desired clinical event. Alternatively, the inventive method may be utilized to gauge the test subject's reaction to the patient's sample versus the test subject's reaction to the third party. This is made possible by simply reversing the comparison of the parameters, that is, comparing the test subject's sample to the patient's sample and the third party's sample, and allows a determination of whether the test subject's (e.g., a donor) cells are immunologically reactive to the patient's cells. Therefore the inventive method provides a means of assessing the patient's immunological status on both sides of the reaction, that is, the patient's reaction to the donor's cells, and the donor's reaction to the patient's cells. Thus, the method can be used to assess immunomodulation of the patient vis-à-vis the donor and also the graft vis-à-vis the patient recipient, e.g., to gauge the risk of rejection and also the development of tolerance.

In one embodiment, the clinical event is the titration of a patient's immunosuppression. The titration of immunosuppression can be after organ transplantation, or during a viral or bacterial infection. Further, the titration can be during a viral or bacterial infection after a patient has undergone organ transplantation. In another embodiment the clinical event can be the comparison of one or more immunosuppressive regimens in which the patient is undergoing a first immunosuppressive regimen and another patient or subject is undergoing a second immunosuppressive regimen and the third subject or patient is not undergoing an immunosuppressive regimen.

In another embodiment, the clinical event can be monitoring or assessing the risk of organ rejection, the event of organ rejection, the degree or severity of organ rejection, or graft dysfunction in suspected rejection. In yet another embodiment, the clinical event can be monitoring the severity of one or more bacterial or viral infections. Further, the clinical event can include monitoring the response of a patient to immunosuppressive agents, (such as FK-506) the withdrawal of an immunosuppressive agent, an antiviral agent, or an anti-bacterial agent.

When the patient is an organ transplant recipient, the organ can be bone marrow or a solid organ. Examples of solid organs include liver, intestine, kidney, heart, lung, pancreas, and sections and combinations thereof.

When the patient's response to an infectious agent is being monitored, the infectious agent can be one or more bacteria and/or viruses. Viruses that elicit an immune response or suppress immune response are contemplated, and include Epstein-Barr, adenovirus, and cytomegalovirus. Additional infectious agents include bioterrorism agents such as anthrax, botulism, etc.

In yet another embodiment, the patient's immune response is assessed by comparing multiple parameters in the reaction of the patient's sample that has been exposed to the test sample (the test reaction), with the patient's sample exposed to the third party (the third party reaction), in order to determine the patient's immune status. In general, if the patient's sample is more reactive to the test sample than the third party sample, an increased risk of rejection, in a transplant patient, is likely. In contrast, if the patient's sample is less reactive to the test sample than the third party sample then a reduced risk of rejection is likely. In another example, a greater degree of proliferation in a highly activated memory phenotype of T-helper cells within the test reaction compared to that of the third party reaction can indicate a heightened risk of rejection in an organ transplant patient. In another example, a lower degree of proliferation in a highly activated memory phenotype of T-helper cells within the test reaction compared to that of the third party reaction can indicate a lower risk of rejection in an organ transplant patient. In another example, a greater number of pro-inflammatory-cytokine-producing cells and less suppressive-cytokine-producing cells within the test reaction than that of the third party reaction can indicate a heightened risk of rejection in an organ transplant patient. Alternatively, a lesser number of pro-inflammatory-cytokine-producing cells and more suppressive-cytokine producing cells within the test reaction compared to that of the third party reaction can indicate a reduced risk of rejection in an organ transplant patient.

Additionally, many cytokines respond in a dose-dependent fashion to anti-rejection drugs. Therefore, a clinician can utilize the patient's own internal targets (these responsive cytokines) to establish a threshold of treatment (i.e., the ¼, ½, and ¾-maximal inhibition) unique to the patient. That is, the method allows therapy to be tailored to the patient and the endpoint of therapy to be determined.

The comparison of reactions is not limited to the ratio of test subject versus third party. For instance precursor frequencies of reactive cells in the parent population, or the absolute numbers of cells of a given subtype, or an absolute number of cells of a given subtype expressed as a fraction of the absolute number of cells of another subtype can be determined. For example, when precursor frequencies are measured, if the precursor frequencies of the test subject-reactive subpopulations, classified by multiple parameters, exceeds a threshold value it can indicate an enhanced risk of rejection. Alternatively, if the precursor frequencies of the test subject-reactive subpopulations, classified by multiple parameters, falls below a threshold value, it can indicate a reduced risk of organ rejection in a transplant patient.

In another embodiment, the inventive method allows multiple parametric measurements of the patient's cell populations at different time points. For example, measurements can be made before, during and after an immunosuppressive regimen, before and after treatment with an anti-infectious agent, or alternatively, before and then after organ transplantation. For example, multiple parametric measurements of the patient's cell subpopulations can be measured at different time points between two or more consecutive doses of an anti-rejection drug. The measurements can be used to define the upper (safe) and lower (effective) limits of the anti-rejection drug therapy for that patient. In this way, an immunosuppressive dosing regimen can be tailored to the patient taking into account his or her unique and dynamic host response to the transplanted organ as well as to the immunosuppressive agents. For instance, suppression of a patient's immune system can be titrated utilizing an immunoreactivity index, such as mixed lymphocyte reaction (MLR). Essentially, the information can be interpreted such that if the ratio of the test subject to third party reactivity is greater than 1, then the FK level, that is the dose of FK-506 (i.e., PROGRAF®, Astellas Pharma US Inc.) required by the patient for adequate immunosuppression, is likely to be above 10 ng/ml, such as up to 20 ng/ml. If the ratio is less than 1, then the FK level is likely to be in the 7-8 ng/ml range.

Additionally, the inventive method can be utilized to determine whether the response to drug therapy indicates resolution of rejection risk. It can also be used to test whether the reduction of drug therapy increases the risk of rejection and whether drug therapy, if discontinued, should be resumed. This provides a powerful tool for the clinician such that over-medication and under-medication of a given patient can be avoided and duration of treatment can be tailored to the needs of the patient. Therefore the clinician would no longer have to rely on general doses and time courses that tend to work in the greater transplant population.

In another embodiment, the effect of the patient's immune system on the test subject's immune system can be determined. This is possible because the invention provides a method for assessing the status of the cell populations in each sample, that is the patient's sample, the test sample, and the third party sample, both before and after they have been reacted together. For example, if the donor cell populations are inhibited by the patient's cells, then the patients' immune system has developed regulatory or immunomodulatory capabilities, that is, anti-rejection properties. Patients who have achieved a state of "tolerance" require less anti-rejection medication and therefore knowledge of this state is particularly useful when treating these patients. Conversely, if no such anti-rejection property has been achieved, the patient has not developed tolerance and therefore that patient's anti-rejection therapy should not be reduced.

As noted above, the power of the inventive method is limited by the number of lasers and detectors available to conduct flow cytometry. However, in the event that one is interested only in a small fraction of the utility of the assay, then a small part of the assay can suffice. For example, equipped with only a 4-color flow cytometer, it is still possible to detect rejection risk by using 4 parameters—one each for recipient CD4, recipient memory (CD45RO), and recipient intravital labeling (CFSE). The donor and third party stimulator cell can be excluded by labeling with a marker that is present on all types of PBL (CD45). However, the assay would require a 3-4 day incubation. Increasing the number of parameters permits a more rapid detection. For example, using a 5- or 6-color flow cytometer, CD25 can be added as a parameter. In this case, the recipient CD4+CD45RO+CD25+ cell can proliferate rapidly in response to the donor or third-party cell (labeled with CD45). Such an assay can show donor-specific proliferation within 1-2 days.

In another embodiment, the invention provides a method of assaying the immune response of a test subject (or patient) to a viral antigen. In accordance with the method, an antigen derived from a virus-of-interest is labeled with a dye-conjugated MHC-tetramer. Also, a tissue sample comprising CD8+ cells is obtained from the test subject, and CD8+ within the sample are exposed to the labeled viral antigen. Thereafter, the cells are assayed to identify any CD8+ cells that also carry the dye to which the MHC-tetramer is conjugated. Typically, this is achieved by flow cytometry, using one dye that labels CD8 and the dye-conjugated MHC-tetramer. The presence of such dually-reactive cells indicates that the immune system of the patient is responsive to the viral antigen. The method can serve as a basis for identifying individuals at risk for contracting an infection from such virus (by the absence of dually-reactive CD8+ cells) and those who can be expected to mount an effective immune response if challenged by the virus.

In another embodiment, the invention provides a method of assaying donor-specific alloreactivity, which can be use to assess a test subject's (recipient's) risk of rejection of tissue from a donor. In accordance with this aspect of the invention, the method comprises first obtaining a tissue sample from the test subject (recipient) and exposing cells within the tissue sample to class I and class II MHC antigens. Thereafter, the lymphocytes from the test subject are assayed to assess whether they have become activated as a result of exposure to the MHC I and MHC II antigens (for example, by screening for presence of CD154, CD95, and/or CD71). Activation of the cells from the test subject is indicative that the test subject is at risk of rejecting tissue form the donor. This approach requires knowledge of recipient and donor HLA antigens (tissue typing) in much the same manner as the cell-cell mixed lymphocyte response. The difference is that one has to pick commercially available/or custom synthesized MHC peptides from a commercial or custom library.

EXAMPLE 1

The examples further illustrate the invention but, of course, should not be construed as in any way limiting its scope.

This example demonstrates the rapid detection of donor-specific alloreactivity with highly activated memory T-helper cells in CFSE-MLR with 7-color flow cytometry.

The participating subjects were sixteen liver transplant patients (LTx), ages ranging from 0.45-18 years, with thymoglobulin (5 mg/kg) induction and undergoing Tacrolimus monotherapy. Peripheral lymphocytes (PBL) from each subject were stained with 1 μM carboxyfluorescein diacetate succimidyl ester (CFSE), and incubated for 24 hours with irradiated donor (HLA-DR matched) and third-party (HLA-DR unmatched) PBL at a 1:1 ratio. Frequencies of naïve (CDR45RA+), memory (CDR45RO+) and double-positive (CD45RA+RO+) CD4+, CD8+, and CD19+ cells expressing the activation marker CD25 to varying degrees (CD25hi, CD25lo, CD25neg) were measured by 7-color flow cytometry. Each lymphocyte subset (CD4+, CD8+, and CD19+) was thus divided into 9 subpopulations. For each of the 27 subphenotypes (e.g. CD4+25hiRO+), cells demonstrating >3-fold dilution of CFSE in daughter cells, due to activation-induced proliferation, were measured. The immunoreactivity index (IR) for each phenotype was calculated as the multiple by which donor-induced proliferation exceeded that due to third-party. This was correlated with a similar index determined by 5-day, 3H-thymidine MLR (mixed lymphocyte reaction). An IR>1 reflected increased rejection risk. An IR<1 reflected decreased rejection risk. An IR derived from both types of MLR was correlated.

The study found 8 non-rejecting subjects, 7 rejecting subjects, and one subject removed from immunosuppression due to PTLD (post-transplant lymphoproliferative disorder). The IR calculated by the proliferative response of CD4+ hiCD45RO-cells in CFSE-MLR correlated well with the IR calculated by 5-day MLR (regression (r2)=0.60). The correlation between the remaining 26 subpopulations of T- and B-cells evaluated in CFSE-MLR and 5-day MLR was poor (r2 values ranging from 0.004 to 0.21). The 5-day MLR demonstrated IR<1 in 7 of the 8 non-rejecting subjects, the subject with PTLD, and 2 of the 7 rejecting subjects. CFSE-MLR based on CD4+CD25hiCD45RO+ cells indicated increased rejection risk (IR>1) in 6 of the 7 rejecting subjects after the rejecting episode and in 2 of the 8 non-rejecting subjects during the first 60 days after LTx. The subject with PTLD and 6 of the 8 non-rejecting subjects demonstrated an IR<1 in CFSE-MLR (CD4+ CD25hiCD45RO+).

The study demonstrates that memory T-helper cells, which express high amounts of the activation marker CD25 can express donor-specific alloreactivity more rapidly, and as effectively as classical 3H-thymidine MLR, which can facilitate rapid identification of rejection risk and safer strategies to minimize clinical immunosuppression.

EXAMPLE 2

The example demonstrates donor-specific immunoreactivity can be measured rapidly by proliferation of activated, memory T-helper cells in flow cytometric, CFSE-MLR.

To evaluate the proliferation of CFSE-labeled recipient T-helper (TH) subsets, co-cultured with HLA-DR matched (donor, D) and mismatched (third-party, TP) lymphocytes (PBMC) in subjects with primary liver transplants were evaluated. Thirty LTx recipients, ages 0-18 years, were pretreated with 5 mg/kg thymoglobulin, and steroid-free Tacrolimus monotherapy. Naïve (CD45RA+) or memory (CD45RO+) CD4+ cells, with or without an activation marker (CD25hi, CD25lo, CD25neg) were enumerated by flow cytometry pre-LTx, and at 1, 3, 6, and 12 months post-LTx in 14 non-rejecting subjects and in 16 rejecting subjects. Thereafter, TH-proliferation was measured by CFSE-dilution using 5-color flow cytometry in 10/30 recipients, after 24-hour co-culture with D- and TP-PBMC. Subpopulations demonstrating ≥3-fold dilution of CFSE were used to calculate immunoreactivity to donor relative to TP (D-TH proliferation: TP-TH proliferation) in TH subsets.

Results of classical MLR with 3H-thymidine incorporation after 5-day co-culture were expressed as the ratio of Donor Stimulation Index (DSI): TPSI and correlated with immunoreactivity measured by CFSE dilution. A significant depletion in CD24hiCd45RO+TH cells in the first 6 months after LTx in rejecting subjects was seen (Mean absolute counts per mm3: Pre-LTx was 62 vs. 24 in month 1 (p=0.047), vs. 6 in month 2 (p=0.01), vs. 17 in months 4-6 (p=0.35)). A significant depletion was also seen in absolute counts of both naïve and memory TH cells that were CD25neg in rejecting subjects. Despite a numeric decrease from pre-LTx counts, such differences were not statistically significant in non-rejecting subjects. Good correlations were seen between DSI:TPSI ratio measured by MLR and Donor: TP TH cell proliferation by CFSE-dilution in memory TH cells which were CD25hi, CD25lo, and CD25neg (r2=0.72, 0.91, and 0.88 respectively). Furthermore, donor-specific immunoreactivity measured by MLR and CFSE-proliferation of CD25hiMemoryTH cells, exceeded immunoreactivity to TP in rejecting subjects, but was less than TP in non-rejecting subjects.

This study demonstrates that memory TH cells expressing high amounts of the activation marker CD25 can represent a rapid and sensitive measure of donor-specific immunoreactivity, which could be used to titrate immunosuppression to the rejection risk in a given patient.

EXAMPLE 3

This example demonstrates the relationship of immunosuppressive drug levels to MLR results.

In this study, 37 children receiving thymoglobulin, and Tacrolimus/Sirolimus (TAC/SRL) monotherapy were observed. Serial measurements tested whether resolution of the risk of acute cellular rejection (ACR-risk) could be defined by (median±SEM) time to achieve: (1) Normal Graft function (SGOT/SGPT<40 IU/ml, Tbili<2 mg/di), (2) "Low" immunosuppression (TAC/SRL level<8 ng/ml), and (3) Immunoreactivity index (IR)<1 in 3H-thymidine MLR. This was the multiple by which recipient response to donor (HLA-DR-matched) lymphocytes exceeded response to third-party (HLA-DR-mismatched). An IR>1 reflected increase, while IR<1 reflected decreased ACR-risk. The median age was 4 years (range 0.45-18 years), and follow-up 570 days (range 106-1144). 20 subjects experienced biopsy-proven early ACR and 17 did not. Compared with non-rejecting subjects, rejecting subjects demonstrated significantly greater (p<0.05, Kaplan-Meier) median time to achieve IR<1, TAC/SRL<8 ng/ml and significantly more recurrent/delayed ACR (35% vs 6%, p=0.032). No such differences occurred for graft function. Also, SEM values suggested a 4-fold greater variation in median time to decreased ACR-risk (IR<1) in rejecting subjects compared with non-rejecting subjects. TAC/SRL levels were 4±0.6 ng/ml at recurrence, due to clinical misjudgment (n=6) and non-compliance (n=2). In two rejecting subjects, recurrence was associated with IR 1.1 and 2.1.

This study demonstrates that during immunosuppression minimization in children, the risk of liver graft rejection can be related to increased immunosuppression requirements and persistent donor-specific immunoreactivity, but not to graft function. Serial monitoring of immunoreactivity can reduce this risk, especially among rejecting subjects.

EXAMPLE 4

This example demonstrates that memory Th proliferative responses can be used to measure rejection risk.

Ten T-cell sub-phenotypes have been evaluated for their ability to measure the instantaneous risk of rejection in 43 children with liver and small bowel transplantation (LTx, SBTx).

Methods: The subject population included 39 immunosupressed children with LTx (n=28) or small bowel transplantation (SBTx, n=15) all of whom had received rabbit antihuman thymocyte globulin and steroid-free Tacrolimus. Also included were 4 children with LTx, in whom the rejection-free course was maintained without any immunosuppression (tolerant). The assay system comprises mixed lymphocyte coculture, in which the indicator of proliferation is dilution of the intravital dye, carboxyflouresciensuccinimydyl ester (CFSE).

Recipient peripheral blood lymphocytes (PBL) which have been purified by Ficoll gradient, are incubated alone, or with PBL from donor or third-party, for a period of 1-4 days, at a ratio of 1:1. The incubation conditions include 37 degrees Centigrade, routine culture medium with 5-10% fetal calf serum, and 5% carbon dioxide. Recipient PBL proliferation is measured in the parent T-helper (Th, CD4+) and T-cytotoxic (Tc, CD8+) cells, and their memory, naïve, activated, and activated-memory subphenotypes using multicolor flow cytometry. Examples of markers for each of these subphenotypes are CD45RO+(memory), naive (CD45RO- or CD45RA-), activated (CD25+) and activated memory (CD45RO+CD25+). The youngest generations of proliferating CFSE-labeled recipient PBL constitute the indicator of alloreactivity. This indicator is measured in each subphenotype. Dead cells are excluded with 7-AAD labeling. Pre-labeling of stimulator donor and third-party cells by anti-CD45-APC or anti-CD45-Pacific Blue prevents admixture with responder cells during analysis. The risk of rejection is equated with donor PBL-induced proliferation, but expressed as a fraction of simultaneously measured, third-party-induced proliferation of recipient PBL. This type of indexing is done to minimize intrapatient variability that may arise from non-alloantigenic stimuli, because such stimuli have an equal likelihood of influencing both, donor-specific and third-party alloresponses on any given day. The resulting immunoreactivity index reflects a higher risk of rejection if >1 and a lower risk of rejection if <1.

Results (Tables 1-2): Immunosupressed children experiencing allograft rejection within the first 60 days after transplantation (n=24) demonstrated a significantly higher immunoreactivity index in memory T-helper cells, when compared with children who have been rejection-free on maintenance immunosuppressants (n=15, 1.29±0.8 vs 0.5±0.22, p=0.0012, corrected for simultaneous measurement of 10 subphenotypes). Significantly higher immunoreactivity index in memory T-helper cells was also seen when rejectors (immunosuppressed) were compared with tolerant children (1.29±0.8 vs 0.421.29±0.80.11, corrected p=0.00034). Parent Th and Tc cells demonstrate borderline significance, which disappears after correction for multiple testing (Tables 1 and 2). Naïve Th cells appear to be significantly more hyporesponsive to donor-alloantigen among tolerant patients, when compared with non-rejectors who are immunosuppressed (immunoreactivity index 0.28±0.12 vs 0.68±0.29, corrected p=0.015).

CONCLUSIONS

Together, these observations support the use of memory Th proliferative responses in measuring instantaneous rejection risk in transplant recipients. If measured longitudinally in individual recipients, the simultaneous evaluation of immunoreactivity indices within memory and naïve Th cells may improve the safety with which immunosuppressants are minimized or eliminated after transplantation.

TABLE 1

Immunoreactivity indices for $CD_4$+ cell and its subphenotypes in LTx children.

| | | $CD_4$+ Parent | Memory | Activated-Memory | Naïve | Activated |
|---|---|---|---|---|---|---|
| Rejectors (R) | | 1.18 ± 0.92 | 1.29 ± 0.81 | 1.11 ± 0.91 | 2.6 ± 6.29 | 3.33 ± 5.7 |
| Non-Rejectors (NR) | | 0.85 ± 0.24 | 0.5 ± 0.22 | 0.59 ± 0.34 | 0.68 ± 0.29 | 0.73 ± 0.25 |
| Tolerant (TOL) | | 0.73 ± 0.18 | 0.42 ± 0.11 | 1.2 ± 0.82 | 0.28 ± 0.12 | 1.33 ± 1.14 |
| R vs NR | p value | 0.119 | 0.000119 | 0.02699 | 0.148531 | 0.069776 |
| | corrected | 1 | 0.001194 | 0.269897 | 1 | 0.697763 |
| R vs TOL | p value | 0.32218874 | 3.4E−05 | 0.855689 | 0.08491 | 0.197708 |
| | corrected | 1 | 0.00034 | 1 | 0.849102 | 1 |
| NR vs TOL | p value | 0.32218874 | 0.371333 | 0.241982 | 0.001517 | 0.457012 |
| | corrected | 1 | 1 | 1 | 0.015171 | 1 |

TABLE 2

Immunoreactivity indices for $CD_3$+ $CD_4$− (T-cytotoxic/CD8+) cell and subphenotypes in LTx children.

| | | CD8+ Parent | Memory | Activated-Memory | Naïve | Activated |
|---|---|---|---|---|---|---|
| Rejectors(R) | | 1.91 ± 1.7 | 1.77 ± 1.49 | 1.54 ± 1.73 | 1.49 ± 1.83 | 1.55 ± 1.32 |
| Non-Rejectors (NR) | | 0.92 ± 0.43 | 0.83 ± 0.47 | 0.93 ± 0.6 | 0.7 ± 0.27 | 0.82 ± 0.58 |
| Tolerant (TOL) | | 0.73 ± 0.3 | 0.56 ± 0.09 | 1.28 ± 0.78 | 0.73 ± 0.79 | 0.48 ± 0.45 |
| R vs NR | p value | 0.03311915 | 0.033734 | 0.2177 | 0.104818 | 0.089756 |
| | corrected | 0.33119154 | 0.337342 | 1 | 1 | 0.897556 |
| R vs TOL | p value | 0.01494483 | 0.007425 | 0.691887 | 0.230728 | 0.078566 |
| | corrected | 0.14944834 | 0.074249 | 1 | 1 | 0.785658 |
| NR vs TOL | p value | 0.36166837 | 0.070162 | 0.532643 | 0.934819 | 0.447136 |
| | corrected | 1 | 0.701618 | 1 | 1 | 1 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A method of assessing the reaction of a patient's immune system to an antigen stimulant, comprising:
    contacting a first sample comprising T-cells obtained from the patient with a viable antigen under conditions sufficient to induce T cell proliferation by the viable antigen;
    contacting a second sample comprising T-cells obtained from the patient with a viable third-party antigen under conditions sufficient to induce T- cell proliferation by the viable third-party antigen;
    measuring T cell proliferation induced by the viable antigen in the first sample by detecting a plurality of markers in the first sample following contacting the first sample with the viable antigen, and at least one additional marker, respectively, wherein the plurality of makers comprises CD154, CD45RO and CD8;
    measuring T cell proliferation induced by the viable third party antigen in the second sample by detecting the plurality of markers in the second sample following contacting the second sample with the third-party antigen, and the at least one additional marker, respectively; and
    comparing T cell proliferation induced by the viable antigen in the first sample to T cell proliferation or an immune response induced by the viable third-party antigen in the second sample,
    thereby determining that the patient's immune system responds to the viable third party antigen and that the viable third party antigen induces reaction of the patient's immune system.

2. The method of claim 1, wherein the additional marker is PD-1, PD-L1, ICOS, or IFN-gamma.

3. The method of claim 2, further comprising assessing viability of T-cells in the first sample and viability of T-cells in the second sample.

4. The method of claim 3, wherein assessing viability of T-cells comprises use of a cell viability dye.

5. The method of claim 4, wherein the cell viability dye is ethidium monoazide (EMA) or 7-amino-actinomycin D (7-AAD).

6. The method of claim 1, wherein the first sample and the second sample are peripheral blood lymphocytes or peripheral blood leukocytes.

7. The method of claim 1, wherein the patient is a human.

8. The method of claim 7, wherein the patient is an adult.

9. The method of claim 7, wherein the patient is a child.

10. The method of claim 1, wherein the plurality of markers further comprises one or more of CD45RA, CD27, CD62, CD28, CCR4, CCR5, CD34, CD134, HLA-DR, CD11c, CD123, CD3, CD4, CD16/56, CD19, CD14, ILT3, CD25, 7-AAD, CD69, CD71, CD86, IL-2, TNF alpha, CFSE, TGF-beta, Annexin V, CFSE, a caspase, IL10, IL-12, IL-2, CCR7, CD56, and CD54.

11. The method of claim 1, wherein the viable antigen or the viable third party antigen comprise an antigenic peptide, an antigenic peptide labeled with a flourochrome, or a combination thereof.

12. The method of claim 1, wherein the T-cells are T-helper or T-cytotoxic lymphocytes.

13. The method of claim 1, wherein the first sample and the second sample are further contacted with an immunomodulatory drug.

14. The method of claim 13, wherein the immunomodulatory drug is an anti-rejection agent.

15. The method of claim 1, wherein the viable antigen is an autoantigen, viral peptide, bacterial peptide, antigen attached to tetramer, or an antigenic peptide attached to a monomeric protein, polymeric protein or peptide.

16. The method of claim 1, wherein the the at least one additional marker is-CTLA4, IFN-gamma.

17. The method of claim 1, wherein the at least one additional marker is PD-1 or PD-L1.

18. The method of claim 1, wherein the at least one additional marker is IFN-gamma.

* * * * *

UNITED STATES PATENT AND TRADEMARK OFFICE
CERTIFICATE OF CORRECTION

PATENT NO. : 10,371,696 B2
APPLICATION NO. : 15/678994
DATED : August 6, 2019
INVENTOR(S) : Rakesh Sindhi Page 1 of 1

It is certified that error appears in the above-identified patent and that said Letters Patent is hereby corrected as shown below:

In the Claims

Claim 16, Column 16, Line 53, "wherein the the a least one" should read --wherein the at least one--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*